United States Patent [19]

Winkel et al.

[11] Patent Number: 5,306,337
[45] Date of Patent: Apr. 26, 1994

[54] ALGINATE IMPRESSION COMPOSITIONS

[75] Inventors: Jens Winkel, Cologne; Reiner Voigt, Leverkusen; Norbert Weber, Cologne, all of Fed. Rep. of Germany

[73] Assignee: Bayer Aktiengesellschaft, Leverkusen, Fed. Rep. of Germany

[21] Appl. No.: 945,197

[22] Filed: Sep. 15, 1992

[30] Foreign Application Priority Data

Sep. 25, 1991 [DE] Fed. Rep. of Germany ....... 4131839

[51] Int. Cl.⁵ .......................... A61K 6/08; A61K 6/10
[52] U.S. Cl. ...................................... 106/35; 523/109
[58] Field of Search ........................... 106/35; 523/109

[56] References Cited

U.S. PATENT DOCUMENTS

| | | |
|---|---|---|
| 2,345,255 | 3/1944 | Gross . |
| 4,381,947 | 5/1983 | Pelico .............. 106/38.5 D |
| 4,394,172 | 7/1983 | Scheuble et al. .............. 106/38.5 D |
| 4,468,484 | 8/1984 | Pellico .................. 523/109 |
| 4,515,913 | 5/1985 | Pellico .................. 523/109 |
| 4,543,372 | 9/1985 | Watanabe et al. ................. 523/109 |
| 4,695,322 | 9/1987 | Schwabe et al. ..................... 106/35 |

FOREIGN PATENT DOCUMENTS

| | | | |
|---|---|---|---|
| 0126824 | 9/1983 | European Pat. Off. ....... | A61K 6/10 |
| 2663641 | 12/1991 | France .......................... | A61K 6/10 |

*Primary Examiner*—Linda Skaling
*Assistant Examiner*—Margaret Einsmann
*Attorney, Agent, or Firm*—Sprung Horn Kramer & Woods

[57] ABSTRACT

The invention relates to a pasty two-component alginate-based material which is used as an impression material in the dental sector.

4 Claims, No Drawings

ALGINATE IMPRESSION COMPOSITIONS

The invention relates to a pasty two-component alginate-based material which is used as an impression material in the dental sector.

Both in the production of inlays, crowns, bridges and prostheses in the dental sector and for corrections of tooth positions and jaw anomalies, a negative of the region in question is produced with the aid of impression compositions and a cast is then made with modelling gypsum. The desired adjustments can then be made with the aid of the gypsum model.

Pulverulent impression compositions of alginates belong to the impression materials which have been used the longest in the dental practice (U.S. Pat. No. 2,345,255). They consist to the extent of 45–70% by weight of fillers (for example diatomaceous earth or silica), 10–20% by weight of alkali metal alginate as the polymer matrix, 8–15% by weight of calcium sulphate dehydrate as a $Ca^{++}$ ion donor, 0.5–4% by weight of alkali metal phosphate ($Na_3PO_4$ or $Na_4P_2O_7$) as a regulator of the processing time, 0.5–4% by weight of fluorides (NaF, $K_2TiF_6$, $K_2ZrF_6$, or $Na_2SiF_6$) for improving the compatibility of the finished impression with the modelling gypsum and 0.1–2% by weight of metal oxides (MgO, ZnO), as well as small amounts of dyestuffs and traces of fragrances.

The powder mixture is preferably prepared in plough blade mixers and is processed by the dentist to a paste with water (20–25 g of powder: 50 ml of water) in a mixing cup by means of a spatula in accordance with the manufacturer's instructions, placed on an impression spoon and pressed onto the part of the jaw of which an impression is to be taken. About 1 minute 45 seconds after the start of mixing in the case of quick-setting alginate impression compositions or 3 minutes in the case of normalsetting alginate impression compositions, the paste suddenly solidifies to a firm rubbery material and the dentist can remove the quite precise impression from the patient's mouth. To avoid a change in the dimensions of this negative mould by evaporation of water, the impression should be filled with an aqueous gypsum slurry after 10 minutes.

However, alginate powders have some serious disadvantages in their processing: a marked tendency to form dust, demixing of the powders due to different densities of the raw materials, metering inaccuracies due to compaction of the powder, cumbersome processing and contamination of the workplace. The tendency of the powder mixtures to form dust can be reduced by additions such as polyethylene glycol and/or polypropylene glycol (U.S. Pat. No. 4,394,172), surface-active substances and hydrocarbons, such as squalane, squalene, decane, dodecane (DE 3 439 884) or specific isoparaffins (EP 0 217 270).

There has therefore been no lack of attempts to develop alginate formulations which do not have the other disadvantages. Setting alginate compositions which consist of components A and B in the form of a pasty two-component system and set after these have been mixed are thus described in DE 31 35 567 and U.S. Pat. No. 4,381,947 and 4,468,484.

According to Examples 1–4, component A can contain:

| | |
|---|---|
| 11–12 | parts by weight of sodium alginate or potassium alginate |
| 50–84 | parts by weight of diatomaceous earth |
| 0.5–2 | parts by weight of $K_4P_2O_7$ or $Na_4P_2O_7$ |
| 0–4 | parts by weight of diethylene glycol or propylene glycol |
| 0–5 | parts by weight of dextrose or sorbitol |
| 150 | parts by weight of water |
| Traces | of preservative |
| Traces | of flavouring substances |

According to Examples 1–4 and 6 a–f, component B can consist of:

| | |
|---|---|
| 0–10 | parts by weight of MgO, ZnO |
| 10–60 | parts by weight of $CaSO_4 \times 2H_2O$, $ZnSO_4$ |
| 2–4 | parts by weight of $K_4P_2O_7$ or $Na_4P_2O_7$ |
| 35–60 | parts by weight of glycerol, propylene glycol, diethylene glycol, mineral oil or oleyl alcohol |
| 0–5 | parts by weight of silicone oil |
| 0–22 | parts by weight of diatomaceous earth, silicon dioxide, talc |
| 0–2 | parts by weight of NaF, $ZnF_2$ |

Although the problem of demixing and dust formation no longer exists with these pastes, as it does with the alginate powders, storage leads to a drastic deterioration in the properties of the product. DE 31 35 567 has thus stated that after mixing of freshly prepared component A and freshly prepared component B in a volume ratio of 4:1, the crosslinked composition has a compressive strength after setting of 900 g/6.45 cm$^2$ (=0.14 kp/cm$^2$ =0.014 N/mm$^2$). 30 days after the components have been prepared, the compressive strength of the crosslinked composition prepared therefrom has already dropped to 600 g/6.45 cm$^2$ (=0.09 kp/cm$^2$=0.009 N/mm$^2$). This inadequate storage stability has also contributed to the fact that paste-like alginate compositions have hitherto been unable to achieve a substantial share of the alginate market.

The invention relates to alginate-based impression compositions consisting of two paste components, characterised in that the constituents which change adversely from the use aspect in the presence of water are contained in the anhydrous paste A and the constituents which do not change adversely from the use aspect in the presence of water, and water, are contained in paste B, that is to say storage-stable pasty 2-component alginatebased impression materials, in which constituents such as the alkali metal alginate, calcium sulphate dehydrate, alkali metal phosphate, fluorides and metal oxides are introduced into a paste A and inert fillers are introduced into a paste B. Bases for paste A are glycerol, glycols, polyethylene glycols and polypropylene glycols and mixtures of these in other anhydrous substances. Gel-forming agents are employed in the water-based paste B, on the one hand to prevent sedimentation of the fillers and on the other hand so that, by adjusting the viscosity to that of paste A, subsequent easy mixing with this paste is ensured.

Such gel-forming agents are, for example, methylcellulose, hydroxypropylcellulose, hydroxyethylcellulose, carboxymethylcellulose and alkali metal polyacrylates and copolymers.

The pastes thus obtained have outstanding processing properties and are stable on storage.

Preferred impression compositions according to the invention are characterised in that paste A comprises a) 10–25% by weight of calcium sulphate dihydrate

| | |
|---|---|
| -continued | |
| b) 15-23% by weight | of potassium alginate and/or sodium alginate |
| c) 3-7% by weight | of metal oxide (MgO, ZnO) |
| d) 0.5-3% by weight | of alkali metal phosphate ($Na_4P_2O_7$, $Na_3PO_4$, $K_4P_2O_7$) |
| e) 0.5-2% by weight | of coloured pigment and |
| f) 50-65% by weight | of paste-forming agent |
| and in that paste B comprises | |
| g) 75-85% by weight | of demineralised water |
| h) 15-25% by weight | of diatomaceous earth or silica |
| i) Traces | of fragrances and |
| j) 0.3-1% by weight | of gel-forming agent. |

After paste A and paste B have been mixed in a weight and/or volume ratio of 1:3.5 to 1:10, a ready-to-use impression composition which sets to a firm rubbery composition within 1 minute 15 seconds to 3 minutes is obtained.

The starting substances a)–e) and h)–i) are generally known and are described in many textbooks and patent documents.

The paste-forming agents f) are glycerol, glycols, polyethylene glycols and polypropylene glycols. Polyethylene glycols having average molecular weights of 300 to 4000 are preferred, and mixtures of these are particularly preferred.

Gel-forming agents j) are carboxymethyl-, methyl-, hydroxyethyl- and hydroxypropylcellulose and alkali metal polyacrylates. Alkali metal salts of polyacrylic acid and polyacrylamide-polyacrylic acid are preferred, and sodium salts of acrylic acid-acrylamide copolymers, such as ®HOSTACERIN PN 73 (Hoechst) are particularly preferred.

The impression compositions according to the invention are distinguished by a good storage stability, the alkali metal alginate in paste A suffering no molecular degradation. By varying the contents of alkali metal phosphate, the desired later setting time can be adjusted in a controlled manner, before the pulverulent contents are processed with polyethylene glycol to give paste A. The gel-forming agent in paste B prevents sedimentation of the fillers and brings the paste into the same viscosity range as paste A.

Good miscability of the two pastes when used is thus achieved. The impression compositions according to the invention meet the requirements of specifications ADA 18 and ISO 1563-2 for alginate impression compositions.

The following example, in which all the parts denote parts by weight, illustrates the invention:

Paste A 14 parts of calcium sulphate dehydrate, 5 parts of magnesium oxide, 19 parts of sodium alginate, 1.5 parts of tetrasodium pyrophosphate, 3.5 parts of potassium fluorotitanate and 1 part of coloured pigment are ground with one another in a bead mill. 40 parts of polyethylene glycol having an average molecular weight of 400 are initially introduced into a planetary mixer and are mixed with the abovementioned powder mixture to form a homogeneous paste. 16.5 parts of the polyethylene glycol are then added and incorporated. The paste is prepared in the absence of moisture.

Paste B 0.5 part of ®HOSTACERIN PN 73 (Hoechst) and 2.5 parts of diatomaceous earth are premixed. This premixture is stirred with a further 18 parts of diatomaceous earth in 79 parts of demineralised water to form a homogeneous paste.

Paste A was mixed with paste B in a weight ratio of 1:4.5. The mixture was tested in accordance with the specification ISO 1563-2.

| Testing | immediately after preparation of the pastes | 90 days after preparation of the pastes |
|---|---|---|
| Setting time | 1 min. 30 secs. | 1 min. 35 secs. |
| Permanent deformation | 2.8% | 3.1% |
| Compressive strength | 0.82 N/mm$^2$ | 0.76 N/mm$^2$ |

We claim:

1. An alginate-based dental impression composition which is stable in the absence of a preservative, comprising two separate and distinct paste components A and B, A being anhydrous and comprising constituents which change adversely in the presence of water, and B comprising water and constituents which do not change adversely in the presence of water, B being present in 3.5 to 10 times the weight of A, wherein paste A consists essentially of
   a) 10–25% by weight of calcium sulphate dihydrate
   b) 15–23% by weight of at least one of potassium alginate and sodium alginate
   c) 3–7% by weight of a metal oxide
   d) 0.5–3% by weight of an alkali metal phosphate
   e) 0.5–2% by weight of colored pigment and
   f) 50–65% by weight of an organic paste-forming agent and paste B comprises
   g) 75–85% by weight of demineralized water
   h) 15–25% by weight of diatomaceous earth or silica
   i) Traces of fragrances and
   j) 0.3–1% by weight of gel-forming agent.

2. A composition according to claim 1, wherein the metal oxide of A(c) is selected from the group consisting of MgO and ZnO and the alkali metal phosphate of A(d) is selected from the group consisting of $Na_4P_2O_7$, $Na_3PO_4$ and $K_4P_2O_7$.

3. A dental impression composition according to claim 1, wherein the paste-forming agent f) in paste A is glycerol, a glycol, a polyethylene glycol or a polypropylene glycol, and the gel-forming agent j) in paste B is carboxymethyl-, methyl-, hydroxyethyl- or hydroxypropylcellulose or an alkali metal salt of an acrylic acid polymer or copolymer.

4. A dental impression composition according to claim 3, wherein the paste-forming agent in paste A is a polyethylene glycol having an average molecular weight of 300 to 4000, and the gel-forming agent j) in paste B is an alkali metal salt of polyacrylic acid or polyacrylamide-polyacrylic acid.

* * * * *